United States Patent
Limbach et al.

(10) Patent No.: US 10,829,433 B2
(45) Date of Patent: *Nov. 10, 2020

(54) METHOD FOR PRODUCTION OF METHYL METHACRYLATE BY OXIDATIVE ESTERIFICATION USING A HETEROGENEOUS CATALYST

(71) Applicants: Rohm and Haas Company, Collegeville, PA (US); Dow Global Technologies LLC, Midland, MI (US)

(72) Inventors: Kirk W. Limbach, Dresher, PA (US); Christopher D. Frick, Pottstown, PA (US); Victor Sussman, Midland, MI (US); Wen-Sheng Lee, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/634,414

(22) PCT Filed: Jun. 25, 2018

(86) PCT No.: PCT/US2018/039229
§ 371 (c)(1),
(2) Date: Jan. 27, 2020

(87) PCT Pub. No.: WO2019/022884
PCT Pub. Date: Jan. 31, 2019

(65) Prior Publication Data
US 2020/0172465 A1    Jun. 4, 2020

Related U.S. Application Data

(60) Provisional application No. 62/538,254, filed on Jul. 28, 2017.

(51) Int. Cl.
| | | |
|---|---|---|
| *C07C 67/39* | (2006.01) | |
| *B01J 21/04* | (2006.01) | |
| *B01J 23/44* | (2006.01) | |
| *B01J 23/52* | (2006.01) | |
| *B01J 35/00* | (2006.01) | |
| *B01J 35/02* | (2006.01) | |

(52) U.S. Cl.
CPC ............. *C07C 67/39* (2013.01); *B01J 21/04* (2013.01); *B01J 23/44* (2013.01); *B01J 23/52* (2013.01); *B01J 35/008* (2013.01); *B01J 35/0066* (2013.01); *B01J 35/0093* (2013.01); *B01J 35/023* (2013.01); *B01J 35/026* (2013.01)

(58) Field of Classification Search
CPC .......... C07C 67/39; C07C 45/75; C07C 69/54
See application file for complete search history.

(56) References Cited

U.S. PATENT DOCUMENTS

| | | |
|---|---|---|
| 4,249,019 A | 2/1981 | Tamura et al. |
| 4,518,796 A | 5/1985 | Aoshima et al. |
| 4,520,125 A | 5/1985 | Baer et al. |
| 5,892,102 A | 4/1999 | Mikami et al. |
| 5,969,178 A | 10/1999 | Okamoto et al. |
| 6,040,472 A | 3/2000 | Yamamatsu et al. |
| 6,228,800 B1 | 5/2001 | Yamaguchi et al. |
| 7,326,806 B2 | 2/2008 | Hayashi et al. |
| 8,461,373 B2 | 6/2013 | Suzuki et al. |
| 8,614,349 B2 | 12/2013 | Yokota et al. |
| 9,511,351 B2 | 12/2016 | Feaviour |
| 9,617,199 B2 | 4/2017 | Krill et al. |
| 2010/0249448 A1 | 9/2010 | Suzuki et al. |
| 2016/0251301 A1 | 9/2016 | Krill et al. |
| 2016/0280628 A1 | 9/2016 | Krill et al. |

FOREIGN PATENT DOCUMENTS

| | | |
|---|---|---|
| CN | 1931824 A | 3/2007 |
| WO | 2015091173 | 6/2015 |
| WO | 2017084969 | 5/2017 |

*Primary Examiner* — Jafar F Parsa
(74) *Attorney, Agent, or Firm* — Brian L. Mutschler

(57) ABSTRACT

A method for preparing methyl methacrylate from methacrolein and methanol. The method comprises contacting a mixture comprising methacrolein, methanol and oxygen with a heterogeneous catalyst comprising a support and a noble metal, wherein said catalyst has an average diameter of at least 200 microns and at least 90 wt % of the noble metal is in the outer 50% of catalyst volume.

9 Claims, No Drawings

METHOD FOR PRODUCTION OF METHYL METHACRYLATE BY OXIDATIVE ESTERIFICATION USING A HETEROGENEOUS CATALYST

BACKGROUND OF THE INVENTION

The invention relates to a method for preparing methyl methacrylate from methacrolein and methanol using a heterogeneous catalyst.

Heterogeneous catalysts having noble metals concentrated in an outer region of the catalyst are known, see, e.g., U.S. Pat. No. 6,228,800. However, there is a need for larger catalyst particles with noble metals more highly concentrated near the surface.

SUMMARY OF THE INVENTION

The present invention is directed to a method for preparing methyl methacrylate from methacrolein and methanol; said method comprising contacting a mixture comprising methacrolein, methanol and oxygen with a heterogeneous catalyst comprising a support and a noble metal, wherein said catalyst has an average diameter of at least 200 microns and at least 90 wt % of the noble metal is in the outer 50% of catalyst volume.

DETAILED DESCRIPTION OF THE INVENTION

All percentage compositions are weight percentages (wt %), and all temperatures are in ° C., unless otherwise indicated. A noble metal is any of gold, platinum, iridium, osmium, silver, palladium, rhodium and ruthenium. More than one noble metal may be present in the catalyst, in which case the limits apply to the total of all noble metals. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Preferably, the support is a particle of an oxide material; preferably γ-, δ-, or θ-alumina, silica, magnesia, titania, zirconia, hafnia, vanadia, niobium oxide, tantalum oxide, ceria, yttria, lanthanum oxide or a combination thereof. Preferably, in portions of the catalyst comprising the noble metal, the support has a surface area greater than 10 $m^2/g$, preferably greater than 30 $m^2/g$, preferably greater than 50 $m^2/g$, preferably greater than 100 $m^2/g$, preferably greater than 120 $m^2/g$. In portions of the catalyst which comprise little or no noble metal, the support may have a surface area less than 50 $m^2/g$, preferably less than 20 $m^2/g$.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the catalyst particle include spheres, cylinders, rectangular solids, rings, multi-lobed shapes (e.g., cloverleaf cross section), shapes having multiple holes and "wagon wheels;" preferably spheres. Irregular shapes may also be used.

Preferably, at least 90 wt % of the noble metal(s) is in the outer 40% of catalyst volume (i.e., the volume of an average catalyst particle), preferably the outer 35%, preferably in the outer 30%, preferably in the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal(s) is within a distance from the surface that is no more than 15% of the catalyst diameter, preferably no more than 10%, preferably no more than 8%, preferably no more than 6%. Distance from the surface is measured along a line which is perpendicular to the surface.

Preferably, the noble metal is gold or palladium; preferably gold.

Preferably, the average diameter of the catalyst particle is at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 4 mm. The average diameter of the support and the average diameter of the final catalyst particle are not significantly different.

Preferably, the amount of noble metal as a percentage of the noble metal and the support is from 0.2 to 5 wt %, preferably at least 0.5 wt %, preferably at least 0.8 wt %, preferably at least 1 wt %, preferably at least 1.2 wt %; preferably no more than 4 wt %, preferably no more than 3 wt %, preferably no more than 2.5 wt %.

Preferably, the catalyst is produced by precipitating the noble metal from an aqueous solution of noble metal salt in the presence of the support. In one embodiment of the invention, the catalyst is produced by incipient wetness in which an aqueous solution of a suitable noble metal precursor salt is added to a porous inorganic oxide such that the pores are filled with the solution and the water is then removed by drying. Preferred noble metal salts include tetrachloroauric acid, sodium aurothiosulfate, sodium aurothiomalate, gold hydroxide, palladium nitrate, palladium chloride and palladium acetate. The resulting material is then converted into a finished catalyst by calcination, reduction, or other treatments known to those skilled in the art to decompose the noble metal salts into metals or metal oxides. Preferably, a $C_2$-$C_{18}$ thiol comprising at least one hydroxyl or carboxylic acid substituent is present in the solution. Preferably, the $C_2$-$C_{18}$ thiol comprising at least one hydroxyl or carboxylic acid substituent has from 2 to 12 carbon atoms, preferably 2 to 8, preferably 3 to 6. Preferably, the thiol compound comprises no more than 4 total hydroxyl and carboxylic acid groups, preferably no more than 3, preferably no more than 2. Preferably, the thiol compound has no more than 2 thiol groups, preferably no more than one. If the thiol compound comprises carboxylic acid substituents, they may be present in the acid form, conjugate base form or a mixture thereof. The thiol component also may be present either in its thiol (acid) form or its conjugate base (thiolate) form. Especially preferred thiol compounds include thiomalic acid, 3-mercaptopropionic acid, thioglycolic acid, 2-mercaptoethanol and 1-thioglycerol, including their conjugate bases.

In one embodiment of the invention, the catalyst is produced by deposition precipitation in which a porous inorganic oxide is immersed in an aqueous solution containing a suitable noble metal precursor salt and that salt is then made to interact with the surface of the inorganic oxide by adjusting the pH of the solution. The resulting treated solid is then recovered (e.g. by filtration) and then converted into a finished catalyst by calcination, reduction, or other treatments known to those skilled in the art to decompose the noble metal salts into metals or metal oxides.

The catalyst of this invention is useful in a process for producing methyl methacrylate (MMA) which comprises treating methacrolein with methanol in an oxidative esterification reactor (OER). The present invention is further directed to a catalyst bed which comprises the catalyst particles and a liquid phase comprising methacrolein, methanol and MMA. The catalyst particles in the catalyst bed typically are held in place by solid walls and by screens. In some configurations, the screens are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101 to 14 MPa); preferably no more than 2000 kPa, preferably no more than 1500 kPa. Preferably, the catalyst bed is in a tubular continuous reactor or a continuous stirred tank reactor; preferably a tubular continuous reactor; preferably the bed is cylindrical or a cylindrical shell. Preferably, the catalyst bed further comprises oxygen gas.

The OER typically produces MMA, along with methacrylic acid and unreacted methanol. Preferably, methanol and methacrolein are fed to the reactor containing the fixed bed in a methanol:methacrolein molar ratio from 1:10 to 100:1, preferably from 1:2 to 20:1, preferably from 1:1 to 10:1. Preferably, the fixed bed further comprises inert materials. Preferred inert materials include, e.g., alumina, clay, glass, silica carbide and quartz. Preferably the inert materials are in the size range for the catalyst or smaller. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts.

EXAMPLES

Catalyst 778: "Egg Shell" Gold Catalyst
0.3088 g of sodium aurothiomalate was dissolved in 8.908 g of DI water with stirring. Next, 10.0243 g of alumina (3.2 mm spheres, Norpro SA6275, Lot No. 2016910048) which had previously been stored in a drying oven at 120° C. were placed in a ceramic crucible. The aqueous gold salt was added drop-wise with periodic stirring using a spatula until the incipient wetness point of the support was reached.

The resulting material was dried for 1 hour at 120° C. and then calcined in a muffle furnace at 300° C. (5° C./min ramp) for 4 hours. The resulting purple catalyst spheres were then stored in an amber vial until ready for use. Elemental analysis via NAA revealed the following elemental composition:

| Description | Au, wt % | Na, ppm | Cl, ppm |
| --- | --- | --- | --- |
| Catalyst 778 | 1.38 ± 0.05 | 1000 ± 30 | 340 ± 20 |

Catalyst 780: Uniform Gold Catalyst (Comparative)
0.3918 g of sodium aurothiosulfate hydrate was dissolved in 9.0567 g of DI water. A 10.0368 g sample of alumina (3.2 mm spheres, Norpro SA6275, Lot No. 2016910048) which had previously been stored in a drying oven at 120° C. was placed in a ceramic crucible. The aqueous gold salt was added drop-wise with periodic stirring using a spatula until the incipient wetness point of the support was reached.

The resulting material was dried for 1 hour at 120° C. and then calcined in a muffle furnace at 300° C. (5° C./min ramp) for 4 hours. The resulting purple catalyst spheres were then stored in an amber vial until ready for use. Elemental analysis via NAA revealed the following elemental composition:

| Catalyst ID | Description | Au Precursor | Calcination Temp (° C.) | Calcination Time (hrs) |
| --- | --- | --- | --- | --- |
| 778 | 1.5 wt % Au, 3.2 mm $Al_2O_3$ | sodium aurothiomalate (I) | 300 | 4 |
| 780 | 1.5 wt % Au, 3.2 mm $Al_2O_3$ | gold (I) sodium thiosulfate hydrate | 400 | 4 |

EDS scans of the catalysts were done with the following results.
Catalyst 780 (comparative)

| wt % Au | Distance in microns from outer edge of the catalyst | Volume % of the catalyst |
| --- | --- | --- |
| 95 | 750 | 85% |
| 90 | 680 | 81% |

The data for Catalyst 780 show that 90 wt % of the gold is within 680 microns of the outer edge, corresponding to the outer 81% of catalyst volume; and that 95 wt % is within 750 microns, or the outer 85%.

Catalyst 778

| wt % Au | Distance in microns from outer edge of the catalyst | Volume % of the catalyst |
| --- | --- | --- |
| 95 | 75 | 13.4% |
| 90 | 70 | 12.6% |

The data for Catalyst 778 ("egg-shell") show that 90 wt % of the gold is within 70 microns of the outer edge, corresponding to the outer 12.6% of catalyst volume; and that 95 wt % is within 75 microns, or the outer 13.4%.

Catalyst Testing

Catalysts were evaluated in a continuous fixed-bed reactor operated in trickle flow mode. In each case, approximately 0.5 g of catalyst was mixed with silicon carbide grit to ensure uniform wetting. The catalyst bed was sandwiched between layers of glass beads. The reactor was operated at 60° C. and 160 psig (1200 kPa) with an inlet oxygen composition of 6 (achieved with 20 sccm air and 50 sccm He) or 21 mol % $O_2$ at a gas flow rate of 70 sccm. Liquid feed (10 wt % methacrolein in methanol) was introduced at a flow rate of 0.07 mL/min. Performance over time, MMA rate as a space time yield, and MIB content (ppm on a 100% MMA basis) are shown in the table below.

|  | Oxygen level fed to reactor [mol %] | Space-Time Yield [mol MMA/kg cat/hr] | Product MIB on a 100% MMA basis [ppm] |
| --- | --- | --- | --- |
| "Egg-shell" metal loading (#778) | 6 | 4 | 504 |
|  | 21 | 4 | 423 |
| Predominately uniform metal loading (#780) (comparative) | 6 | 1 | 740 |
|  | 21 | 2 | 405 |

The data show that at high oxygen levels formation of byproduct MIB is low. However, at low oxygen levels, such as those that exist towards the end of a catalyst bed where the oxygen is depleted, the inventive "egg-shell" catalyst provides a greatly reduced level of MIB. The space-time yield for the inventive catalyst is superior at both oxygen levels, but especially at low oxygen level.

The invention claimed is:

1. A method for preparing methyl methacrylate from methacrolein and methanol; said method comprising contacting a mixture comprising methacrolein, methanol and oxygen with a heterogeneous catalyst comprising a support and gold, wherein said catalyst has an average diameter of at least 300 microns and at least 90 wt % of the gold is in the outer 50% of catalyst volume.

2. The method of claim 1 in which the catalyst has an average diameter from 400 microns to 10 mm.

3. The method of claim 2 in which the catalyst is contained in a catalyst bed.

4. The method of claim 3 in which the catalyst bed is at a temperature from 40 to 120° C.

5. The method of claim 4 in which pH in the catalyst bed is from 4 to 10.

6. The method of claim 5 in which at least 90 wt % of the gold is in the outer 40% of catalyst volume.

7. The method of claim 1 in which the support is selected from the group consisting of γ-, δ-, or θ-alumina, silica, magnesia, titania, vanadia, ceria, lanthanum oxide and a combination thereof.

8. The method of claim 7 in which methanol and methacrolein are fed to a reactor containing the catalyst bed in a molar ratio from 1:1 to 10:1, respectively.

9. The method of claim 8 in which at least 95 wt % of the gold is in the outer 30% of catalyst volume.

* * * * *